United States Patent [19]

Schoenwald et al.

[11] Patent Number: 5,157,044

[45] Date of Patent: Oct. 20, 1992

[54] ANALOGS OF CARBONIC ANHYDRASE INHIBITORS AND THEIR USE AS TOPICAL IOP INHIBITORS

[75] Inventors: Ronald D. Schoenwald; Charles F. Barfknecht, both of Iowa City, Iowa

[73] Assignee: University of Iowa Research Foundation, Iowa City, Iowa

[21] Appl. No.: 535,573

[22] Filed: Jun. 11, 1990

Related U.S. Application Data

[63] Continuation-in-part of Ser. No. 503,855, Apr. 3, 1990, abandoned, which is a continuation-in-part of Ser. No. 410,982, Sep. 22, 1989, Pat. No. 5,095,026, which is a continuation-in-part of Ser. No. 464,063, Feb. 4, 1983, Pat. No. 4,975,449.

[51] Int. Cl.$^5$ .................. C07D 285/135; A61K 31/41
[52] U.S. Cl. ..................................... 514/363; 548/139
[58] Field of Search .......................... 548/139; 514/363

[56] References Cited

U.S. PATENT DOCUMENTS 5,010,204  4/1991  Antonaroli .......................... 548/139

FOREIGN PATENT DOCUMENTS 354881  2/1990  European Pat. Off. ............ 548/134

OTHER PUBLICATIONS

Maren, J. Pharmacol. Exp. Ther. 241, 56,(1987) Abstract.
Vaughan, J. Org. Chem. 21, 700(1956) Abstract.

Primary Examiner—Robert Gerstl
Attorney, Agent, or Firm—Zarley, McKee, Thomte, Voorhees & Sease

[57] ABSTRACT

Analogs are prepared of the carbonic anhydrase inhibitors methazolamide, and dichlorphenamide. The analogs link a cleavable functional group to the pharmacologically active carbonic anhydrase inhibitor resulting in compounds of improved corneal permeability, which are non-irritable to the eye and which are effective topically to inhibit intraocular pressure.

7 Claims, No Drawings

5,157,044

ANALOGS OF CARBONIC ANHYDRASE INHIBITORS AND THEIR USE AS TOPICAL IOP INHIBITORS

CROSS-REFERENCE TO RELATED APPLICATIONS

This application is a continuation-in-part of co-pending and commonly owned application Ser. No. 503,855 filed Apr. 3, 1990, now abandoned which is a continuation-in-part of Ser. No. 410,982 filed Sep. 22, 1989 entitled PRODRUGS OF CARBONIC ANHYDRASE INHIBITORS now U.S. Pat. No. 5,095,026, which itself is a continuation-in-part of co-pending and commonly owned application Ser. No. 464,063 filed Feb. 4, 1983, now U.S. Pat. No. 4,975,449 and entitled TOPICAL TREATMENT FOR GLAUCOMA.

BACKGROUND OF THE INVENTION

Glaucoma, which some estimate affects 2 million adults over 40, is an impairment of vision caused by too much fluid pressure within the eye.

Surgical treatment for glaucoma is effective; however, it is expensive and some surgeons will use surgery only as a last resort.

Carbonic anhydrase inhibitors, prescribed orally, work well to treat this disease, but they carry a host of side effects, for nausea to kidney stones.

Glaucoma stems from an excess of fluid behind the cornea, the three-layered tissue that acts as a window to let light enter. Fluid carrying nutrients such as potassium and glucose constantly wash the inside of the cornea to keep it healthy, much as tears wash the outside of the cornea.

In some middle-aged adults, fluids build up faster than can be absorbed back into the blood, for one of two reasons: the ciliary body (a tiny tissue behind the iris) may excrete too much fluid, or the fluid may not drain off at the normal rate.

Either way, the excess fluid damages the optic nerve. At first a glaucoma victim usually experiences a subtle loss of peripheral vision—objects will seem to disappear from certain spots to the side. But glaucoma often leads to middle-age blindness.

Unfortunately, the two approaches to general drug usage in treating glaucoma—topical (dropped into the eye) and oral—each have a peculiar set of side effects.

To make the long journey, oral drugs must be dosed in very high concentration. One class of drugs, called carbonic anhydrase inhibitors, slow the formation of fluid by inhibiting a chemical reaction at the ciliary body. Along with their well-tested effectiveness comes nausea, tingling in fingers and toes, and other side effects. Oral drugs generally do not, however, cause side effects in the eye.

Certain topical drugs, while causing less systemic effects, on the other hand, can cause severe headaches and constrict the pupil, making the daytime appear dark.

In our earliest parent application, analogs of 2-benzothiazole-sulfonamides are prepared as carbonic anhydrase inhibitors. While many of the compounds that are prepared are carbonic anhydrase active, in fact some have limited practical usage because the compounds do not penetrate the cornea very rapidly and/or may not distribute very well to the active site, i.e., ciliary body of the eye. This is not only true for certain carbonic anhydrase inhibitor active 2-benzothiazolesulfona-mides, but it is also true for certain other carbonic anhydrase inhibitors such as methazolamide/acetazolamide analogs and dichlorphenamide analogs. In our application entitled PRODRUGS OF CARBONIC ANHYDRASE INHIBITORS, we prepared prodrugs of 2-benzothiazolesulfona-mides, methazolamide and dichlorphenamide analogs. This application is based upon the discovery that with regard to analogs of methazolamide particularly but also dichlorphenamide, the analogs themselves are active and will rapidly penetrate the cornea; therefore there is no need to go the extra step of preparing the prodrug.

Compounds which are carbonic anhydrase active inhibitors but have limited penetrability across the cornea and into the ciliary body are, as a practical matter, of limited value in developing topical carbonic anhydrase inhibitors even though they may inhibit the activity of carbonic anhydrase in vitro, i.e., in a test tube. Put another way, if the compound does not have the correct distribution and penetration properties, its chances of being pharmacologically active carbonic anhydrase inhibitor in patients are small, at best. Thus, it is important if one is developing effective carbonic anhydrase inhibitors which can be topically applied, that the compound not only be active in inhibiting carbonic anhydrase but also reach the active site.

It is a primary objective of the present invention to provide analogs of methazolamide and dichlorphenamide as carbonic anhydrase inhibitors with enhanced corneal penetration and ciliary body distribution properties without negatively impacting the carbonic anhydrase activity.

It is another objective of the present invention to prepare analogs of the above mentioned carbonic anhydrase inhibitors, in particular, methazolamide/acetazolamide and dichlorphenamide. The analogs have a high degree of corneal penetrability, and can effectively reach the inside of the eye and inhibit the pharmacologically active carbonic anhydrase inhibitor by enzymatic and/or hydrolytic degradation of a chemical bond between the drug moiety and carbonic anhydrase inhibitor.

An even further objective of the present invention is to prepare and use as topical carbonic anhydrase inhibitor compositions of novel analog compounds derived from methazolamide and dichlorphenamide.

The method and manner of accomplishing each of the above objectives as well as others will become apparent from the detailed description of the invention which follows hereinafter.

SUMMARY OF THE INVENTION

Rapidly penetrating carbonic anhydrase inhibitors are prepared and used to effectively lower IOP. The compounds are highly effective at corneal permeability. As a result, they allow improved topical penetration across the cornea allowing the carbonic anhydrase inhibitor to then function within the eye to reduce intraocular pressure.

DETAILED DESCRIPTION OF THE INVENTION

Inhibition of carbonic anhydrase is one mechanism of action by which the production of aqueous humor can be limited within the eye. If aqueous humor production can be limited, this in turn can be used to control ocular hypertension. Carbonic anhydrase inhibitors can be administered orally to reduce intraocular pressure (IOP), but this route of administration is associated with systemic side effects due to the large doses required to attain therapeutically useful levels in the eye. Topical administration of carbonic anhydrase inhibitors directly to the eye has the advantage of minimizing or eliminating systemic side effects due to the smaller doses required, and the more direct access the drug has to the organ. However, a carbonic anhydrase inhibitor may not produce optimum therapeutic effects, and may not be adequately absorbed or distributed to the active site, or may cause ocular irritation or local side effects as a result of changes of the carbonic anhydrase inhibitor molecule necessary to achieve enhanced corneal penetration and distribution. Thus, in preparing carbonic anhydrase inhibitors, one must constantly balance the activity, that is the effectiveness at inhibiting carbonic anhydrase, against the local or side effects that may be caused by changes necessary in the molecule in order to make it effective within the eye.

In accordance with the present invention, it has been discovered how certain analogs of two distinct classes of carbonic anhydrase inhibitors can be made more effective topically by attachment of functional groups to the carbonic anhydrase inhibitor which, among other things allows for greater lipophilic solubility and for distribution and accumulation at the site of the action. In short, the optimal corneal penetration of the active inhibitor is achieved without topical irritation, and later, when converted to the active carbonic anhydrase inhibitor within the eye, optimum lipid solubility in the tissue is achieved.

The carbonic anhydrase inhibitors which can be used to make the drugs of this invention having a high degree of penetrability of the cornea so that maximum effective delivery of the active carbonic anhydrase inhibitor (CAI) is achieved, include analogs of two basic groups of CAI's: methazolamide analogs and dichlorphenamide analogs. Methazolamide analogs which can be utilized in this invention are methazolamides of the formula:

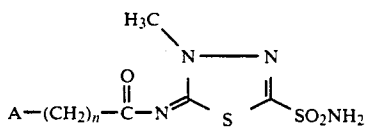

wherein n is from 1 to 5, preferably 1 to 3.

Another class of carbonic anhydrase inhibitors also useful are dichlorphenamide analogs of the formula:

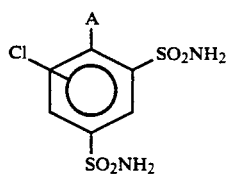

In each of the general formulas given for the methazolamides and dichlorphenamides "A" is a terminal moiety which is attached to the carbonic anhydrase inhibitor which allows it to still retain carbonic anhydrase inhibitory activity, but increases the ability to penetrate the cornea and is a functional group which forms an enzymatically cleavable bond. For the dichlorphenamide analogs the chloro moiety may be attached either ortho or meta to "A".

As used herein, "enzymatically cleavable bond" refers to a bond which can be cleaved after the compound is dropped onto the eye. The cleavage can be by enzymatic cleavage and/or hydrolytic cleavage. As a result, the new compound is formed by covalently linking as pharmacologically active, but insufficiently penetrating, carbonic anhydrase inhibitor to an enzymatically and/or hydrolytically degradable bond, "A", to provide the useful analogs. The drug dissolves in the tears, penetrates the cornea and degrades within the cornea to release the pharmacologically active carbonic anhydrase inhibitor which distributes and accumulates in the ciliary body, and inhibits the enzyme carbonic anhydrase with a resulting decrease in the production of aqueous humor. Thus, intraocular pressure is reduced.

Key aspects of this invention are: First, synthesis of a molecule which inhibits carbonic anhydrase and has less than optimum penetrability and distribution itself. Secondly, the preparation of the carbonic anhydrase inhibitor analog by attachment of the functional group A by a covalent bond such as an ester, carbamate, carbonate, glycoside, etc. which can be degraded by enzymes present in the eye and/or hydrolyzed at physiological pH. Third, the use of the analog to provide enhanced penetrability without any eye irritation caused by the presence of groups such as amine groups which are ionized at physiological pH and hence irritating.

Suitable moieties represented by A include hydroxyalkoxy, preferably $C_1$ to $C_5$ alkyl, and most preferably alkoxyethoxy, simple hydroxy, hydroxy acetamido, glycolyl hydroxy and amine. Others include monosaccharides such as D- and L-glucose. 6-carboxylic acid derivatives of monosaccharides such as D- and L-glucuronic acid, and D- and L-gluconic acid, and the like.

The linkage or covalent bond between A and the carbonic anhydrase inhibitor ring system can be described as a covalent, degradable linkage between the active carbonic anhydrase inhibitor molecule and the terminal group A.

These compounds have greater than 0.25% solubility on a weight/volume basis without significant contributions from ionization at physiological pH. Thus, minimal or no irritation is expected. Also, the carbonic anhydrase inhibitor is a potent inhibitor of the enzyme carbonic anhydrase, and does have significant penetrability in comparison with the compound prior to attachment of the group A. Also, the linkage of A and the CAI can be degraded by enzymes present in the eye such as acetylcholinesterase, serum cholinesterase, glycolase, etc., or can be degraded by hydrolysis/decomposition at physiological pH to release the active carbonic anhydrase inhibitor.

Examples of methazolamide or N-[5-aminosulfonyl)-3-methyl-1,3,4-triadiazol-2(3H)-ylidene[acetamide and its analogs which can be used are the following:

hydroxymethazolamide, N-[5-(aminosulfonyl)-3-methyl-1,3,4-triadiazol-2(3H)-ylidene]hydroxyacetamide and hydroxyethoxymethazolamide, N-[5-(aminosulfonyl)-3-methyl-1,3,4-triadiazol-2(3H)-ylidene]hydroxyethoxyacetamide, and N-[5-(aminosulfonyl)-3-methyl-1,3,4,-thiazol-2(3H)-ylidene]-2-[glycolylhydroxy]acetamide.

Other compounds modified from the parent molecule methazolamide and acetazolamide may also be prepared.

Examples of dichlorphenamide or 4,5-dichloro-m-benzenedisulfonamide which may be made and used are the following:

4-hydroxy-5-chloro-m-benzenedisulfonamide
4-hydroxyethoxy-5-chloro-m-benzenedisulfonamide
4-hydroxyacetamido-5-chloro-m-benzenedisulfonamide
4-hydroxyethoxyacetamido-5-chloro-m-benzenedisulfonamide.

Other 4-amino-6-chloro-m-benzenedisulfonamides; 4-hydroxyacetamido-6-chloro-m-benzenedisulfonamides; 4-hydroxy-6-chloro-m-benzenedisulfonamides; 4-hydroxyethoxy-6-chloro-m-benzenedisulfonamides; 4-chloro-5-hydroxy-m-benzenedisulfonamides; 4-chloro-5-hydroxyethoxy-m-benzenedisulfonamides; 4-amino-5-chloro-m-benzenedisulfonamides; 4-chloro-5-amino-m-benzenedisulfonamides; and 4-chloro-5-hydroxyacemido-m-benzenedisulfonamides may also be used.

An analog of one of the prototype carbonic anhydrase inhibitors (Ethoxyzolamide, Methazolamide, Acetazolamide, or Dichlorphenamide) is designed and synthesized by either total synthesis or by conversion from a commercially available intermediate. The analog is characterized by its carbonic anhydrase inhibitory activity and the presence of a functional group (A). In preferred format A will contain a terminal hydroxyl or amino group and will be covalently linked to the active CAI through a linkage degradable at physiological pH and/or in the presence of normal ocular enzymes.

The following examples are offered to further illustrate but not limit the process of this invention.

EXAMPLE 1

Synthesis of 6-[β-glucopyranosyl)oxyethoxy]-2-benzothiazolesulfonamide

A solution of acetobromoglucose (4.93 g.; 12.0 mmole), 6-[2'-hydroxyethoxy]-2-benzothiazolesulfonamide (2.74 g.; 10.0 mmole), and 2,4,6-collidine (1.09 g.; 9.00 mmole) in dry tetrahydrofuran (50 mL) were added at $-25°$ C. to a suspension of silver triflate (3.60 g.; 14.0 mmole) in dry tetrahydrofuran over a period of 30 minutes. The reaction mixture was stirred overnight at room temperature. Collidine (2 mL) was added and the mixture filtered through paper. The filtrate was washed with aqueous sodium thiosulfate solution, the organic layer separated, and evaporated to dryness at reduced pressure. The solid residue was chromatographed on a silica gel column (300 g.) and eluted with chloroform. The product fractions (UV light and charring positive) were combined and evaporated to dryness at reduced pressure.

The unpurified 6-[2'-(2'',3'',4'',6''-tetra-O-acetyl-β-glucopyranosyl)oxyethoxy]-2-benzothiazolesulfonamide (3.02 g.; 5.00 mmole) was dissolved in anhydrous diethyl ether (100 mL) and combined with cold (0° C.) saturated methanolic ammonia (100 mL) and stirred overnight with the temperature rising to room temperature over a six hour period. The solution was evaporated to dryness at reduced pressure and chromatographed on a silica gel column (150 g.) and eluted with chloroform/methanol (9.1). The product fractions (UV light and charring positive) were combined and evaporated to dryness at reduced pressure, and lyophilized to yield 6-[β-glucopyranosyl)oxyethoxy]-2-benzothiazolesulfonamide. The product conformed to accepted standards of purity and its structural assignment verified by standard spectroscopic methods (mass spec, $^{13}C$ and $^{1}H$ nuclear magnetic resonance).

EXAMPLE 2

Reduction in IOP Following Topical Application of the Compound of Example 1 to Dutch Belt Rabbit Eyes Healthy, Dutch Belt rabbits, accustomed to the experimental procedure, 2-3 months old, of either sex and weighing about 3-4 pounds were placed in restraining boxes. Intraocular pressure (IOP) was measured using a pneumatonograph (Digilabs Model 30D, Cambridge, Mass.) and 1-2 drops of 0.5% proparacaine hydrochloride for anesthesia. IOP is measured in both eyes. The drug of Example 1 is dissolved in a 3% carbomer 940 vehicle (Carbopol 940, B. F. Goodrich, Cleveland, Ohio) and instilled (50 μL) into the lower conjunctival sac of the right eye only.

The "IOP recovery rate assay" as reported by Vareilles and Lotti (Ophthalmic Res., 13, 72-79, 1981) is used. In this assay 20% sodium chloride solution is infused into the marginal ear vein for 10 minutes at a rate of 1 mL/min. This procedure was altered by infusing 10% sodium chloride solution for 15 minutes at a rate of 1 mL/min. to minimize vascular damage. IOP is measured just prior to beginning the infusion and again at 15, 25, 35, 45, 60, 75, 90, 120, 150, 180, and 210 minutes.

The hypertonic sodium chloride solution causes a decline in IOP which then recovers at a rate dependent on the activity of carbonic anhydrase. IOP gradually returns to normal at a constant rate but much more slowly if a carbonic anhydrase inhibitor is present in the eye in sufficient concentration. The return to normal is measured from the positive linear slope which begins at about 45-60 minutes after starting the infusion. The test drug (3% drug in carbomer vehicle) is administered 60 minutes before the start of the sodium chloride solution infusion. Control animals are given vehicle without drug.

Results are expressed as mean values ± standard deviation of the slopes representing recovery of IOP (mm Hg/min.):

| treated rabbits [n = 4 eyes] | control eyes [n = 2 eyes] |
| --- | --- |
| 0.068 ± 0.032 | 0.112 ± 0.0073 |

The % decrease in slope activity due to the drug and compared to the control is 39%. The topically treated rabbit eyes show a statistically slower ($p<0.05$) recovery rate to normal IOP values when compared to control eyes which only received vehicle. This indicates the drug is effective when topically applied to the eye.

Other satisfactory results can also be achieved with the 2-benzothiazolesulfonamide carbonic anhydrase inhibitor of the Examples 1 and 2 is substituted with methazolamide/acetazolamide analogs and dichlorphenamide analogs, in that penetrability is increased, and carbonic anhydrase inhibition is still maintained at effective levels within the eye. This indicates degradation of the linkage between the water soluble carrier and the carbonic anhydrase inhibitor by enzymes within the eye such that the carbonic anhydrase inhibitor continues to exhibit CAI activity.

In these and other examples, as in the parent case, Ser. No. 464,063, the amount of the carbonic anhydrase inhibitor active used in the composition should be from about 0.25% by weight to about 5% by weight of an eye drop test composition, preferably from about 0.5% by weight to about 2.0% by weight. The important point is not the dose amount, but simply that it be an effective carbonic anhydrase inhibiting amount, and yet not such a great amount that side effects will be achieved. Generally, amounts within the range specified are satisfactory.

The diluent for the eye drop composition may be an isotonic eye treatment carrier buffered to a pH of from about 4.0 to about 8.0, and typically it will contain small amounts of conventional wetting agents and antibacterial agents. The preferred pH is within the range of from about 6.8 to about 7.8. Antibacterial agents, where they are included may be within the range of from about 0.004% by weight to about 0.02% by weight of the composition.

The following examples illustrate the preparation of the CAI analogs having the functional group "A" and of their use as effective topical CAI inhibitors.

EXAMPLE 3

Preparation of
N-[5-(aminosulfonyl)-3-methyl-1,3,4-thiadiazol-2(3H)-ylidene]-2-[glycolylhydroxy]acetamide A suspension of 2-imino-3-methyl-2(3H)-1,3,4-thiadiazoline-5-sulfonamide [3.88 g.; 20.0 mmole], obtained by deacylation of methazolamide via the Katritzky procedures [T. H. Maren, A. Bar-Ilan, K. C. Caster, & A. R. Katritzky, *J. Pharmacol. Exp. Ther.*, 24, 56–63 (1987)], and glycolide [1,4-dioxane-2,5-dione; Polysciences, Inc.; 2.32 g.; 20.0 mmole] was stirred in dry pyridine [25 ml] at room temperature for ten days. After 24 hours the suspension became a solution.

The solution was adsorbed on silica gel [25 g.] with the aid of methanol and the pyridine was removed by evaporation at room temperature in a fume hood. The pyridine-free silica gel/reaction mixture was applied to a 200 g. silica gel column. Elution was conducted with a chloroform/methanol mixture [40:1]. The UV-positive fraction was collected [crude yield 50%] and recrystallized from methanol. M.p. 156°–7 C.;

$C_7H_{10}N_4O_6S_2$; MS/CI m/e 311 (MH+); PMR (acetone) 4.00 [s,$CH_3$], 4.20 [s,$CH_2$], 4.90 [s, $CH_2$], 7.50 [br. $HN_2$].

EXAMPLE 4

Preparation of N-[5-(aminosulfonyl)-3-methyl-1,3,4-thiadiazol-2(3H)-ylidene]-2-hydroxypropanamide The synthesis here follow the preparation of Example 3 described above, except propiolactone was used as the acylating agent [in place of glycolide for Example 3, and the yield was 10%.

EXAMPLE 5

Preparation of
N-[5-(aminosulfonyl)-3-methyl-1,3,4-thiadiazol-2-(3H)-ylidene]-2-D-glucuronamide The synthesis of the example follows the preparation of Example 4 described above, except D-glucurono-6,3-lactone was used as the acylating agent [in place of glycolide for Example 4] and the yield was less than 10%.

EXAMPLE 6

Reduction in IOP Following Topical Application of the Compounds SC-1, SC-2 and SC-3 to New Zealand Rabbit Eyes Healthy, New Zealand rabbits, accustomed to the experimental procedure, 2–3 months old, of either sex and weighing about 3–4 pounds were laced in restraining boxes. Intraocular pressure (IOP) was measured using a pneumatonograph (Digilbs Model 30D, Cambridge, Mass.) following the instillation of 1–2 drops of 0.5% proparacaine hydrochloride to both eyes for anesthesia. The drugs of Examples 2, 3, and 4 were dissolved in a pH 6.8–7.2 phosphate buffer and instilled (50 μL) onto the cornea of either eye.

The "IOP recovery rate assay" as reported by Vareilles and Lotti (Ophthalmic Res., 13, 72–79, 1981) was used. IOP was measured just prior to beginning the infusion (20% sodium chloride solution at a rate of 1 mL/min for 10 minutes) and again at 10, 25, 40, 55, 70, 100, 130, 160, and 190 minutes.

The hypertonic sodium chloride solution causes a decline in IOP which then recovers at a rate dependent on the activity of carbonic anhydrase. IOP gradually returns to normal at a constant rate but much more slowly if a carbonic anhydrase inhibitor is present in the eye in sufficient concentration. The return to normal is measured from the positive linear slope which begins at about 30–45 minutes after starting the infusion. The test drug (Examples 3, 4, and 5) were administered 60 minutes before the start of the sodium chloride infusion. Control animals are given vehicle with drug.

If the drug is active the topically treated rabbit eyes show a slower recovery to initial IOP values. The recovery rate is appropriately linear and a slope is measured for the control and treated rabbit eyes. The results are expressed in the table as a percent decrease in slope for the treated eyes compared to the control eyes along with the probability:

TABLE

| Treatment | | % Decrease | Probability |
| --- | --- | --- | --- |
| Ex. 3 | 0.5% (N = 11) | 44 | <0.01 |
| Ex. 3 | 0.25% (N = 17) | 37 | <0.05 |
| Ex. 3 | 0.0125% (N = 12) | 12 | <0.05 |
| Ex. 4 | 1% (N = 14) | 26 | <0.05 |
| Ex. 4 | 3% (N = 9) | 25 | <0.05 |
| Ex. 5 | 0.5% (N = 9) | 34 | <0.05 |

What is claimed is:

1. Analogs of methazolamide carbonic anhydrase inhibitors (CAI) having the formula:

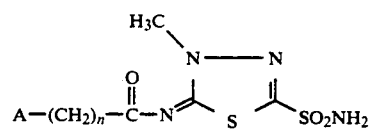

wherein n is from one to five, and A is a hydroxy moiety which when attached to said methazolamide increases its corneal penetration but still allows retention of CAI activity and which also forms an enzymatically or hydrolytically cleavable bond.

2. The compounds of claim 1 wherein n is from one to three.

3. A compound of claim 1 wherein n is one.

4. N-[5-(aminosulfonyl)-3-methyl-1,3,4-thiadiazol-2(3H)-ylidene]-2-hydroxyacetamide.

5. N-[5-(aminosulfonyl)-3-methyl-1,3,4-thiadiazol-2(3H)-ylidene]-2-[glycolylhydroxy]acetamide.

6. A method of reducing intraocular eye pressure, said method comprising:

topically applying to the eye a small but therapeutically effective intraocular eye pressure reducing amount of an analog of methazolamide carbonic anhydrase inhibitor having the formula:

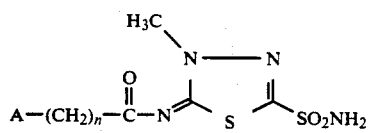

wherein n is from one to five, and A is a hydroxy moiety which when attached to said methazolamide increases its corneal penetration but still allows retention of CAI activity and which also forms an enzymatically or hydrolytically cleavable bond.

7. A topical composition for eye drop treatment comprising:

a small but therapeutically effective intraocular eye pressure reducing amount of an analog of methazolamide carbonic anhydrase inhibitor of the formula:

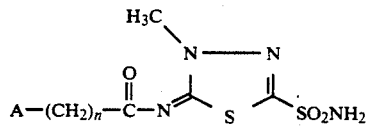

wherein n is from one to five, and A is a hydroxy moiety which when attached to said methazolamide increases its corneal penetration but still allow retention of CAI activity and which also forms an enzymatically or hydrolytically cleavable bond.

* * * * *